United States Patent [19]

Takeda et al.

[11] Patent Number: 5,149,857
[45] Date of Patent: Sep. 22, 1992

[54] PROCESS FOR PRODUCTION OF SULFONIUM COMPOUNDS

[75] Inventors: Mutsuhiko Takeda; Isao Hagiwara; Fumiya Zaima; Shuzabu Sakaguchi, all of Tokyo, Japan

[73] Assignee: Mitsubishi Gas Chemical Company, Inc., Tokyo, Japan

[21] Appl. No.: 530,898

[22] Filed: May 29, 1990

[30] Foreign Application Priority Data

Jun. 7, 1989 [JP] Japan ................. 1-143018
Jul. 20, 1989 [JP] Japan ................. 1-188118

[51] Int. Cl.$^5$ ............................. C07C 69/96
[52] U.S. Cl. ..................... 558/271; 568/18; 568/28; 568/29
[58] Field of Search .............. 558/271; 568/18, 28, 568/29

[56] References Cited

U.S. PATENT DOCUMENTS 4,857,656 8/1989 Kouge ................. 558/271

FOREIGN PATENT DOCUMENTS 0245662 11/1987 European Pat. Off. .
0346756 12/1989 European Pat. Off. .
63-8365 1/1988 Japan .

OTHER PUBLICATIONS

CA 112 (25): 234992h (Jun. 1990).
H. M. Gilow et al., "Substituent Effects of Positive Poles in Aromatic Substitution. II. The Nitration of Sulfonium Salts." Aug. 1967, pp. 2580–2583, Journal of Organic Chemistry, vol. 32.

*Primary Examiner*—Jose G. Dees
*Assistant Examiner*—Barbara S. Frazier
*Attorney, Agent, or Firm*—Frishauf, Holtz, Goodman & Woodward

[57] ABSTRACT

A process for producing sulfonium compounds represented by the general formula (III) which comprises reacting alkylthiophenol derivatives represented by the general formula (I) and dialkyl sulfate represented by the general formula (II).

General Formula (I):

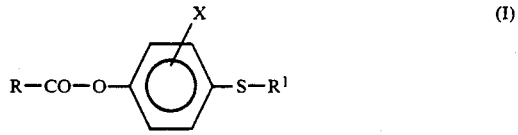

General Formula (II): $(R^2)_2SO_4$
General Formula (III):

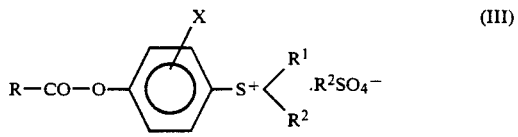

12 Claims, No Drawings

PROCESS FOR PRODUCTION OF SULFONIUM COMPOUNDS

BACKGROUND OF THE INVENTION

1. Field of the Invention

The present invention relates to a process for production of sulfonium compounds and novel methylthiophenol derivatives. More particularly, it is concerned with a process for producing sulfonium compounds, p-dialkylsulfoniophenol derivatives represented by the general formula (III), by sulfoniumating alkylthiophenol deratives represented by the general formula (I) with dialkyl sulfate represented by the general formula (II).

General Formula (I):

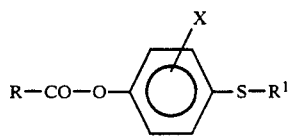

General Formula (II): $(R^2)SO_4$

General Formula (III):

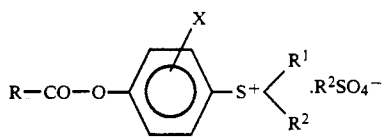

In the general formulas (I), (II) and (III), $R^1$ and $R^2$ may be identical or different and are each a lower alkyl group having 1 to 4 carbon atoms, and X is a hydrogen atom, a halogen atom, or a lower alkyl group having 1 to 4 carbon atoms. In the general formulas (I) and (III), R is an allyloxy group, a 9-fluorenylmethoxy group, a 2,2,2-trichloroethoxy group, or a 2-chlorobenzyloxy group.

Sulfonium compounds represented by the general formula (III) are useful compounds as reagents for introduction of an acyl group as a protecting group to various compounds in the organic chemical field, e.g., synthesis of peptides, because they exhibit acylating action in an aqueous solution.

The term "acyl" as used herein refers to a group as derived by removal of a hydroxyl group from a carbonic acid monoester.

The present invention further relates to novel methylthiophenol derivatives capable of being precursors for the above sulfonium compounds and more specifically to novel methylthiophenol derivatives represented by the general formula (I').

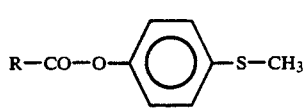

wherein R is the same as defined above.

2. Description of the Related Arts

For the production of the sulfonium compounds represented by the general formula (III), a method of reacting acid halides, i.e., carbonylhalogenide compounds with p-dialkylsulfoniophenol alkylsulfate in the presence of a base has been generally employed.

Japanese Patent Application Laid-Open No. 8365/1988, for example, discloses a method in which acid chloride is used as the acid halide, and triethylamine is used as the base.

This method, however, is not necessarily satisfactory for practical use, because a complicated operation is required for separation and purification of the objective products, sulfonium compounds of the general formula (III), from by-products of triethylamine hydrochloride.

For example, when p-dimethylsulfoniophenol methylsulfate and 9-fluorenylmethoxycarbonyl chloride are reacted in the presence of triethylamine, the yield of the objective 9-fluorenylmethyl p-dimethylsulfoniophenyl carbonate methylsulfate is about 40%, and its purity is as low as 80 to 85%.

The present invention is intended to provide an industrially advantageous process for producing the desired sulfonium compounds with high efficiency and at low production costs by reacting alkylthiophenol derivatives and dialkyl sulfate.

The present inventors made investigations on a method of synthesis of sulfonium compounds represented by the general formula (III) in order to overcome the above problems. As a result, it has been found that the objective sulfonium compounds can be produced with high efficiency, substantially without any complicated purification operations, by reacting alkylthiophenol derivatives represented by the general formula (I) and dialkyl sulfate represented by the general formula (II).

Moreover, in the course of the above investigations, it has been found that specified compounds of the alkylthiophenol derivatives represented by the general formula (I) to be used as the starting material in the above reaction are novel compounds.

Based on the findings, the present invention has been accomplished.

SUMMARY OF THE INVENTION

An object of the present invention is to provide a process for efficiently producing sulfonium compounds represented by the general formula (III).

Another object of the present invention is to provide a process for producing industrially advantageously the above sulfonium compounds substantially without any complicated purification operations and in high yields.

Still another object of the present invention is to provide novel mehtylthiophenol derivatives (or mehtylthiophenyl carbonate).

The present invention relates to a process for producing sulfonium compounds represented by the general formula (III) which comprises reacting alkylthiophenol derivatives represented by the general formula (I) and dialkyl sulfate represented by the general formula (II).

The present invention further relates also to mehtylthiophenol derivatives (or methylthiophenyl carbonate) represented by the general formula (I').

DESCRIPTION OF THE PREFERRED EMBODIMENTS

In the general formula (I), $R^1$ is a lower alkyl group having 1 to 4 carbon atoms, preferably a methyl group or an ethyl group. R is an allyloxy group, a 9-fluorenylmethoxy group, a 2,2,2-trichloroethoxy group, or a 2-chlorobenzyloxy group.

Specific examples of alkylthiophenol derivatives represented by the general formula (I) are allyl p-methylthiophenyl carbonate, 9-fluorenylmethyl p-methylthiophenyl carbonate, 2,2,2-trichloroethyl p-methylthiophenyl carbonate, and 2-chlorobenzyl p-methylthiophenyl carbonate.

As dialkyl sulfates represented by the general formula (II), those in which $R^2$ is a lower alkyl group having 1 to 4 carbon atoms are preferred, and those in which $R^2$ is a methyl group or an ethyl group, and thus which are easily available are more preferred. X is appropriately chosen from a hydrogen atom, a halogen atom and an alkyl group, depending on solubility, acylating reactivity, and so forth of the sulfonium compound of the general formula (III). In general, X is preferably a hydrogen atom. When X is an alkyl group, a lower alkyl group having 1 to 4 carbon atoms is preferred.

Preferred examples of the dialkyl sulfate represented by the general formula (II) are dimethyl sulfate and diethyl sulfate.

In accordance with the process of the present invention, an alkylthiophenol derivative represented by the general formula (I) and dialkyl sulfate represented by the general formula (II) are reacted with each other to convert the alkylthio group of the alkylthiophenol derivative into sulfonium, thereby synthesizing a sulfonium compound of the general formula (III).

One of the features of the present invention is that by-products which are difficult to separate from the desired product are not formed and, therefore, a complicated separation and purification operation after the reaction are substantially not required, making the process very economical.

In accordance with the process of the present invention, an alkylthiophenol derivative represented by the general formula (I) (hereinafter abbreviated to an "MSP compound") and a dialkyl sulfate are reacted by heating with stirring in the presence or in the absence of a solvent. In the practice of the present invention, the order in which the starting materials are added is not critical. For example, after heating a solution of MSP compound, dialkyl sulfate can be added thereto.

The amount of dialkyl sulfate to be used is not limited as long as it is at least one mol per mol of MSP compound. In view of a rate of reaction, it is preferably 5 to 15 mol, more preferably 8 to 12 mol per mol of MSP compond.

As the reaction temperature is higher, the reaction is completed in a shorter time. However, since dialkyl sulfate is decomposed when the reaction temperature is too high, it is generally in a range of 0° to 150° C. and preferably in a range of 40° to 120° C. The end of the reaction can be judged by the disappearance of the MSP compound as determined by high-performance liquid chromatography.

The solvent to be used in the process of the present invention is not critical as long as it does not react with MSP compounds or dialkyl sulfate. For example, aprotic polar solvents such as acetonitrile, esters such as ethyl acetate, ethers such as dioxane, and aromatic hydrocarbons such as toluene can be used. Of these compounds, aprotic polar solvents are preferred, and acetonitrile is one of the most preferred solvents. Two or more solvents can be used in combination.

Although the amount of the solvent used varies with the type of the solvent or the type of the MSP compound, it is generally 0.1 to 10 L (L=liter), preferably 0.5 to 3 L per mol of the MSP compound. Depending on the ratio of the MSP compound to the dialkyl sulfate, the reaction can be carried out without use of a solvent.

After completion of the reaction, the desired product can be easily isolated by adding a poor solvent such as diethyl ether, ethyl acetate, toluene or carbon tetrachloride to the reaction mixture.

The sulfonium compound thus obtained does not contain by-products such as triethylamine hydrochloride, and thus no complicated purifications are required.

In accordance with the process of the present invention, the objective product, sulfonium compound, can be easily obtained by adding a poor solvent to the reaction mixture of alkylthiophenol derivative and dialkyl sulfate. Moreover, the product obtained by the process of the present invention is of high purity and thus needs almost no complicated purification operations which have been required in the conventional methods. As a result, the process is simplified and the production cost is greatly reduced.

Moreover, this sulfonium compound can be used as a highly useful protective reagent because it has an ability to acylate the amino group of amino acid in an aqueous solution.

Among the alkylthiophenol derivatives of the general formula (I), those in which $R^1$ is a methyl group and X is hydrogen, i.e., methylthiophenol derivatives represented by the general formula (I') are novel compounds.

Methylthiophenol derivatives represented by the general formula (I') (hereinafter sometimes abbreviated as "Roc-MSP") can be easily obtained by reacting p-methylthiophenyl chloroformate represented by the formula (IV) (hereinafter sometimes abbreviated as "CF-MSP) and alcohols represented by the formula (V) (hereinafter sometimes referred to merely as "alcohol") in the presence of pyridine in a dichloromethane solvent.

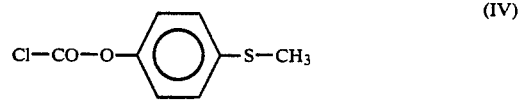
(IV)

R—OH         (V)

In the present invention, the order in which the above starting materials are added is not critical. In general, a solution of pyridine and alcohol in dichloromethane is added dropwise to a dichloromethane solution of CF-MSP. The reaction temperature is suitably 0° to 40° C. The amount of dichloromethane used as a solvent is suitably 0.5 to 3 liters per mol of CF-MSP.

After completion of the reaction, Roc-MSP can be obtained by washing the reaction mixture with water to remove pyridine hydrochlorate and then distilling away dichloromethane from the organic layer. Roc-MSP can be purified by recrystallizing from methanol or hexane, for example, if necessary.

An advantage of using pyridine as a base in the present invention is that the desired product can be obtained with a high yield.

CF-MSP to be used as the starting material for preparation of Roc-MSP is obtained by reacting phosgene with p-methylthiophenol represented by the general formula (VI) (hereinafter sometimes abbreviated as "MSP—OH") in the presence of pyridine as a base.

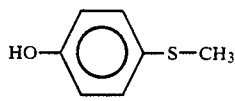

More specifically, CF-MSP is prepared by dropping a dichloromethane solution of MSP—OH and pyridine to a dichloromethane solution containing phosgene in the amount of 1.5 to 5 mol, preferably 2 to 3 mol per mol of MSP—OH, at a temperature of −30° to 10° C., preferably −20° to 0° C.

The amount of dichloromethane used as a solvent is preferably 0.1 to 10 liters, more preferably 0.5 to 3 liters per mol of MSP—OH.

After completion of the reaction, excessive phosgene and dichloromethane as a solvent are distilled away. A solvent incapable of dissolving pyridine hydrochlorate, such as hexane or petroleum ether, is added to the resulting residue to dissolve CF-MSP, and then the pyridine hydrochlorate is removed by filtration. Upon distillation of hexane from the filtrate obtained above, CF-MSP is obtained as an oily material. This CF-MSP can be purified by distilling under reduced pressure, if necessary.

An advantages of using pyridine as a base in the synthesis of CF-MSP is that side reactions are reduced and thus the yield of CF-MSP is high. Another advantage is that since the same solvent and base are used in the subsequent reaction, synthesis of Roc-MSP, CF-MSP can be used as such in the subsequent reaction without isolation thereof. More specifically, the operation of synthesis of Roc-MSP can be carried out continuously without, in particular, an isolation operation of CF-MSP, by distilling away excessive phosgene along with the solvent, supplying the solvent to the reaction solution of CF-MSP, and dropping alcohol and pyridine.

Roc-MSP as obtained above is a stable substance, and no problem arises even if it is stored at room temperature for several months. Roc-MSP can be used as a protective reagent by converting into the corresponding sulfonium compound.

By carrying out the process for production of sulfonium compound according to the present invention using Roc-MSP as a starting material, the desired sulfonium compound of the general formula (III) can be efficiently produced.

The present invention is described in greater detail with reference to the following examples.

PREPARATION EXAMPLE 1

Preparation of Chloroformate

Six hundred ml of dichloromethane was placed in a flask, and 64 ml (99 g, 1.0 mol) of phosgene was introduced thereto while cooling with ice. To the resulting solution, a solution of 100 ml of dichloromethane containing 39.55 g (0.5 mol) of pyridine and 70.10 g (0.5 mol) of p-methylthiophenol was dropped while maintaining the reaction temperature at less than 5° C. After completion of the dropwise addition, the resulting mixture was stirred for one hour while cooling with ice. Then, a distillation apparatus was attached to the flask, which was then heated on a hot water bath maintained at 50° C. to distill away excessive phosgene and part of the solvent. Finally, the remaining solvent was removed under reduced pressure. Then, 700 ml of hexane was added to the residue as obtained above and stirred at room temperature for one hour. Pyridine hydrochlorate precipitated was removed by filtration, and the filtrate was concentrated by the use of an evaporator. Finally the hexane was completely removed in vacuum whereupon 101.5 g of crude p-methylthiophenyl chloroformate was obtained as an oily material.

The purity as determined based on the chlorine content and a high-performance liquid chromatographic analysis was 6.6%. A main impurity contained in the product was residual hexane, and the amount of bis p-methylthiophenyl carbonate was only less than 0.4%.

Upon purification of the crude p-methylthiophenyl chloroformate by distillation under reduced pressure, 86.02 g of pure p-methylthiophenyl chloroformate was obtained (yield 85%).

Boiling point: 96.0°–98.5° C. (0.3 mmHg).

$^1$H-NMR (CDCl$_3$): δ=2.38 (3H, s, S-Me) (Me: methyl), 6.95–7.40

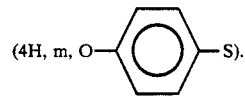

(4H, m, O— —S).

IR (NaCl): 1790 cm$^{-1}$ (C=O).

Elemental Analysis:

|   | Calculated | Found |
|---|---|---|
| C | 47.41% | 47.48% |
| H | 3.48% | 3.31% |
| Cl | 17.49% | 17.36% |

EXAMPLES 1 TO 3

One hundred ml of dichloromethane and 20.27 g (0.1 mol) of p-methylthiophenyl chloroformate prepared in Preparation Example 1 were placed in a flask, and 50 ml of a dichloromethane solution containing 0.1 mol of alcohol shown in Table 1 and 8.70 g (0.11 mol) of pyridine was dropped to the above solution at room temperature. The resulting mixture was then stirred for two hours. The reaction solution was washed with water to remove pyridine hydrochlorate, and the obtained organic layer was concentrated under reduced pressure. Finally, excessive pyridine was removed in vacuum whereupon the objective product shown in Table 1 was obtained. When the product was crystalline, it was purified by recrystallizing from methanol. The results are shown in Table 1. Physical values of each compound are shown in Table 2.

TABLE 1

| Example | Alcohol | Product (Roc-MSP) | Yield (%) | Substance No. |
|---|---|---|---|---|
| Example 1 | Allyl alcohol | Allyl p-methyl-thiophenyl-carbonate | 100 | (1) |
| Example 2 | 9-fluorenyl methanol | 9-fluorenylmethyl p-methylthio-phenyl carbonate | 99 | (2) |
| Example 3 | 2,2,2-trichloro ethanol | 2,2,2-trichloro-ethyl p-methyl-thiophenyl carbonate | 100 | (3) |

TABLE 2

(Physical Values of Roc—MSR)

| Substance No. | m.p. (°C.) | IR | $^1$H-NMR(CDCl$_3$) | Elemental Analysis Calculated | Found |
|---|---|---|---|---|---|
| (1) | Oily | (KBr) 1760 cm$^{-1}$ (C=O) | δ = 2.45(3H, s, S—Me)<br>4.72(2H, d J=5Hz, CH$_2$=CH—CH$_2$)<br>5.15 to 5.58(2H, s, CH$_2$=CH—CH$_2$)<br>5.69 to 6.40(1H, m, CH$_2$=CH—CH$_2$)<br>6.95 to 7.39(4H, m, O—⟨C$_6$H$_4$⟩—S) | C: 58.91%<br>H: 5.39% | 58.66%<br>5.55% |
| (2) | 135.0 to 136.5 | (KBr) 1755 cm$^{-1}$ (C=O) | δ = 2.41(3H, s, S—Me)<br>4.15 to 4.60(3H, m, >CH and CH$_2$)<br>6.89 to 7.82(12H, m, Aromatic) | C: 72.90%<br>H: 5.01% | 72.27%<br>4.77% |
| (3) | 65.0 to 67.0 | (KBr) 1765 cm$^{-1}$ (C=O) | δ = 2.50(3H, s, S—Me)<br>5.06(2H, s, CH$_2$—O)<br>7.31(4H, s, O—⟨C$_6$H$_4$⟩—S) | C: 38.06%<br>H: 2.87% | 38.00%<br>2.91% |

EXAMPLE 4

To a solution prepared by dissolving 101.33 g (0.5 mol) of p-methylthiophenyl chloroformate prepared in Preparation Example 1 and 71.29 g (0.5 mol) of 2-chlorobenzyl alcohol in ml of dichloromethane, 40.34 g (0.51 mol) of pyridine was dropped in such a manner that the reaction temperature did not exceed 30° C.

After completion of dropwise addition, the resulting mixture was stirred at room temperature for 2 hours to complete the reaction. The reaction solution was washed with water, 0.5 N hydrochloric acid, an aqueous sodium hydrogencarbonate solution, and water in this order.

Upon distillation of dichloromethane from the organic layer obtained above under reduced pressure, 154.4 g of the desired 2-chlorobenzyl p-methylthiophenyl carbonate was obtained (yield 100%).

Melting point: 49.5°-50.0° C.

$^1$H-NMR (CDCl$_3$): δ=2.46 (3H, s, S-Me), 5.38 (2H, s, —CH$_2$—O—), 7.00-7.55 (8H, m, Aromatic).

IR (KBr):1755 cm$^{-1}$ (C=O).
Elemental Analysis:

|   | Calculated | Found |
|---|---|---|
| C | 58.35% | 58.19% |
| H | 4.24% | 4.26% |

EXAMPLE 5

Five hundred four point five grams (4.0 mol) of dimethyl sulfate was added to 123.5 g (0.4 mol) of 2-chlorobenzyl p-methylthiophenyl carbonate prepared in Example 4 above and reacted at 60° C. for 3 hours while stirring.

The reaction mixture was cooled to room temperature, and then toluene as a poor solvent was added to crystallize the sulfonium product. The product was 2-chlorobenzyl p-dimethylsulfoniophenyl carbonate methylsulfate, and the amount was 160.5 g (yield 92%).

Melting point: 108°-113° C.

$^1$H-NMR (CDCl$_3$): δ=3.44 (6H, s, $^+$SMe$_2$), 3.68 (3H, s, MeSO$_4^-$), 5.39 (2H, s, —CH$_2$—), 7.20–7.60 (4H, m, 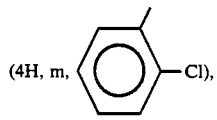), 7.52, 8.18 (4H, each d, J=9.0Hz, 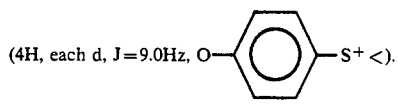).

IR (KBr): 1760 cm$^{-1}$ (C=O).
Elemental Analysis:

|   | Calculated | Found |
|---|---|---|
| C | 46.95% | 46.78% |
| H | 4.40% | 4.45% |

EXAMPLE 6

One point eight one grams (5.0 mmol) of 9-fluorenylmethyl p-methylthiophenyl carbonate obtained in Example 2, 0.70 g (5.5 mmol) of dimethyl sulfate, and 5 ml of acetonitrile were placed in a reactor in this order, and reacted with stirring at 60° C. for 29 hours. The reaction solution was cooled to room temperature and then ethyl acetate as a poor solvent was added thereto to crystallize the sulfonium product. High-performance liquid chromatographic and NMR analyses showed that the product was nearly pure 9-fluorenylmethyl p-dimethylsulfoniophenyl carbonate methylsulfate, and the amount of the product was 2.22 g (yield 91%).

Melting point: 117°-122° C.

$^1$H-NMR (CDCl$_3$): δ=3.42 (6H, s, $^+$SMe$_2$), 3.65 (3H, s, MeSO$_4^-$), 4.16–4.62 (3H, m, —CH$_2$—, and —CH<),
IR (KBr): 1760 cm$^{-1}$ (C=O),
Elemental Analysis:

|   | Calculated | Found |
|---|---|---|
| C | 59.00% | 58.63% |

| | Calculated | Found |
|---|---|---|
| H | 4.95% | 4.90% |

COMPARATIVE EXAMPLE

One hundred eighty ml of dried acetonitrile was added to 12.34 g (46.3 mmol) of p-dimethylsulfoniophenol methylsulfate and 5.13 g (50.7 mmol) of triethylamine to prepare a slurry-like mixture, which was then stirred while cooling with ice. To this mixture, 13.20 g (51.0 mmol) of -fluorenylmethoxycarbonyl chloride dissolved in 30 ml of acetonitrile was dropwise added. The resulting mixture was stirred at 0° C. for 2 hours, and then a white solid of triethylamine hydrochloride was removed by filtration. This solid was washed with a small amount of acetonitrile. Acetonitrile used in this washing was mixed with the filtrate obtained above. This mixture was concentrated under reduced pressure, and then ethyl acetate as a poor solvent was added thereto to crystallize the product. Since the product contained trimethylamine hydrochlorate, it was purified by recrystallization from acetonitrile—ethyl acetate.

The product finally obtained was 9-fluorenylmethyl p-dimethylsulfoniophenyl carbonate methylsulfate. The amount of the product was 9.95 g, and the yield was only 44%.

EXAMPLE 7

One point eight one grams (5.0 mmol) of 9-fluorenylmethyl p-methylthiophenyl carbonate, 6.31 g (50 mmol) of dimethyl sulfate, and 5 ml of acetonitrile were placed in a reactor in this order, and then reacted with stirring at 60° C. for 4 hours.

This reaction solution was cooled to room temperature, and then ethyl acetate as a poor solvent was added thereto to crystallize the sulfonium product. High-performance liquid chromatographic and NMR analyses showed that the product was pure 9-fluorenylmethyl p-dimethylsulfoniophenyl carbonate methylsulfate, and the amount of the product was 2.30 g (yield 94%).

EXAMPLES 8 to 14

The reaction was carried out in the same manner as in Example 7 except that reaction condition shown in Table 3 was selected. After completion of the reaction, ethyl acetate as a poor solvent was added to the reaction mixture to crystallize the sulfonium product. The results are shown in Table 3. High-performance liquid chromatographic and NMR analyses showed that the product was pure 9-fluorenylmethyl p-dimethylsulfoniophenyl carbonate methylsulfate.

TABLE 3

| | (Solvent) Reaction Conditions | | | |
|---|---|---|---|---|
| No. | Solvent | Temperature | Time | Yield |
| Example 8 | Acetonitrile | 40° C. | 25 hr | 88% |
| Example 9 | Acetonitrile | 80° C. | 2 hr | 89% |
| Example 10 | None | 100° C. | 0.5 hr | 96% |
| Example 11 | Ethyl acetate | 60° C. | 6 hr | 95% |
| Example 12 | 1,4-Dioxane | 60° C. | 5 hr | 90% |
| Example 13 | Chloroform | 60° C. | 5 hr | 89% |
| Example 14 | Sulforane | 100° C. | 1 hr | 87% |

In Example 14, the molar ratio of 9-fluorenylmethyl p-methylthiophenyl carbonate to dimethyl sulfate was 1:2, and in Examples 8 to 13, the ratio was 1:10.

APPLICATION EXAMPLE 1

Synthesis of N-(9-fluorenylmethoxycarbonyl)glycine in aqueous solution

Zero point three eight gram (5.08 mmol) of glycine was added to 13.5 ml of a 10% aqueous sodium carbonate solution, and dissolved therein by stirring at room temperature. To this solution, a solution of 2.95 g (6.04 mmol) of 9.-fluorenylmethyl p-dimethylsulfonylphenyl carbonate methylsulfate obtained in each of Examples 7 to 14 in 13.5 ml of water was dropwise added while cooling with ice. After completion of the addition, the resulting mixture was stirred at room temperature for 3 hours. After the reaction was completed, 500 ml of water was added to the reaction solution, which was then washed twice with 75 ml of ether. The formed aqueous layer was cooled with ice, and then hydrochloric acid was added to adjust the pH value of the aqueous layer to 1-2. Insoluble matters precipitated were collected by extracting three times with 150 ml of ethyl acetate. The organic layers thus obtained were collected together and washed with 100 ml of water, and then the organic layer was dried over anhydrous magnesium sulfate as drying agent. After drying, the drying agent was removed by filtration, and ethyl acetate was distilled away under reduced pressure. Upon addition of ether to the residue obtained above, the desired product, N-(9-fluorenylmethoxycaronbyl)glycine, was obtained as white crystals.

Amount: 1.45 g (4.88 mmol, Yield 96%).

Melting point: 172°-174° C. (174°-175° C. in the literature).

EXAMPLE 15

Seven point seven one grams (50 mmol) of diethyl sulfate was added to 1.81 g (5.0 mmol) of 9-fluorenylmethyl p-methylthiophenyl carbonate obtained in Example 2, and the resulting mixture was reacted with stirring at 100° C. for 8 hours. This reaction solution was cooled to room temperature, and then ether as a poor solvent was added thereto to precipitate an oily sulfonium product. This oily product was washed three times with ether and dried under reduced pressure.

High-performance liquid chromatographic and NMR analyses showed that the product was nearly pure 9-fluorenylmethyl p-(S-methyl-S-ethyl) sulfoniophenyl carbonate ethylsulfate, and the amount of the product was 2.30 g (yield 89%).

$^1$H-NMR (dimethylsulfoxide-d$_6$): $\delta$=0.94-1.32 (6H, m, $CH_3CH_2$—S$^+$, $CH_3CH_2SO_4^-$), 3.33 (3H, s, $CH_3$—S$^+$); 3.40-3.90 (4H, m, $CH_3CH_2$—S$^+$, $CH_3CH_2SO_4^-$), 4.20-4.86 (3H, m, >CH—, $CH_2$—O), 7.16-8.32 (12H, m, Aromatic).

IR (KBr): 1760 cm$^{-1}$ (C=O).

Elemental Analysis:

| | Calculated | Found |
|---|---|---|
| C | 60.45% | 60.40% |
| H | 5.46% | 5.51% |

EXAMPLE 16

Twelve point six one grams (100 mmol) of dimethyl sulfate was added to 2.24 g (10.0 mmol) of allyl p-methylthiophenyl carbonate obtained in Example 1, and the resulting mixture was reacted with stirring at 100° C. for 3 hours. This reaction solution was cooled to room temperature, and then ether as a poor solvent was added. The resulting mixture was allowed to stand in a refrigerator to crystallize the sulfonium product.

High-performance liquid chromatographic and NMR analyses showed that the product was nearly pure allyl p-dimethylsulfoniophenyl carbonate methylsulfate, and the amount of the product was 3.15 g (yield 90%).

Melting point: 82°–86° C., $^1$H-NMR (DMSO-d$_6$): δ=3.35 (6H, s, +SMe$_2$), 3.62 (3H, s, MeSO$_4$$^-$), 4.69 (2H, d, J=6Hz, CH$_2$=CH—CH$_2$—O), 5.20–5.52 (2H, m, CH$_2$=CH—CH$_2$—O), 5.72–6.20 ($^1$H, m, CH$_2$=C$\underline{H}$—CH$_2$—O), 7.42, 8.10 (4H),

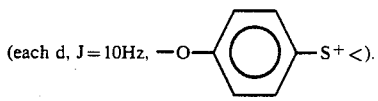

(each d, J=10Hz, —O—⟨⟩—S$^+$<).

IR (KBr): 1760 cm$^{-1}$ (C=O).
Elemental Analysis:

|   | Calculated | Found |
|---|---|---|
| C | 44.56% | 44.18% |
| H | 5.18% | 4.93% |

EXAMPLE 17

Twelve point six one grams (100 mmol) of dimethyl sulfate was added to 3.16 g (10 mmol) of 2,2,2-trichloroethyl p-methylthiophenyl carbonate, and the resulting mixture was reacted with stirring at 100° C. for 3 hours. This reaction solution was cooled to room temperature, and ether as a poor solvent was added. The resulting mixture was allowed to stand in a refrigerator to crystallize the sulfonium product. The product was 2,2,2-trichloroethyl p-dimethylsulfoniophenyl carbonate methylsulfate, and the amount of the product was 4.20 g (yield 95%).

Melting point: 126°–131° C.

$^1$H-NMR (DMSO-d$_6$): δ=3.39 (6H, s, +SMe$_2$), 3.48 (3H, s, MeSO$_4$$^-$), 5.13 (2H, d, Cl$_3$CH$_2$—O), 7.73, 8.27 (4H),

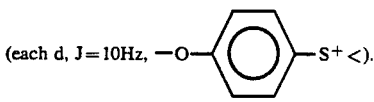

(each d, J=10Hz, —O—⟨⟩—S$^+$<).

IR (KBr): 1780 cm$^{-1}$ (C=O)
Elemental Analysis:

|   | Calculated | Found |
|---|---|---|
| C | 32.63% | 32.55% |
| H | 3.42% | 3.49% |

What is claimed is:

1. A process for producing a sulfonium compound of the formula

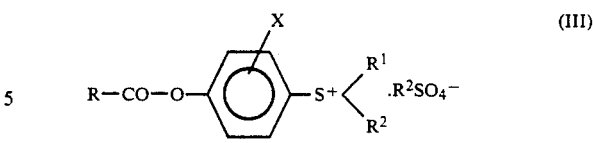

which comprises reacting an alkylthiophenol compound of the formula

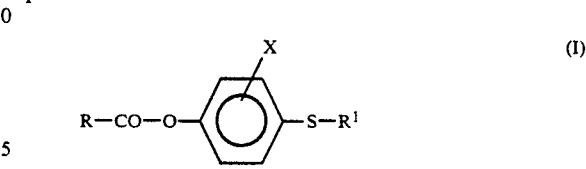

and a dialkyl sulfate of the formula

in an amount of 1 to 15 moles of the dialkyl sulfate per mole of the alkylthiophenol compound and at a temperature of 0° to 150° C., wherein R$^1$ and R$^2$ are identical or different and are each an alkyl group having 1 to 4 carbon atoms, X is a hydrogen atom, a halogen atom, or an alkyl group having 1 to 4 carbon atoms, and R is an allyloxy group, a 9-fluorenylmethoxy group, or a 2,2,2-trichlorethoxy group.

2. The process as claimed in claim 1, wherein the alkylthiophenol compound of the formula (I) is at least one compound selected from the group consisting of allyl p-methylthiophenyl carbonate, 9-fluoromethyl p-methylthiophenyl carbonate and 2,2,2-trichloroethyl p-methylthiophenyl carbonate.

3. The process as claimed in claim 1, wherein the dialkyl sulfate of the formula (II) is dimethyl sulfate or diethyl sulfate.

4. The process as claimed in claim 1, which further comprises the reaction being carried out in the presence of a solvent.

5. The process as claimed in claim 4, wherein the solvent is at least one compound selected from the group consisting of aprotic polar solvents, esters, ethers, and aromatic hydrocarbons.

6. The process as claimed in claim 4, wherein the solvent is at least one compound selected from the group consisting of acetonitrile, ethyl acetate, and dioxane.

7. The process as claimed in claim 4, wherein the amount of the solvent is 0.1 to 10 liters per mol of the alkylthiophenol compound of the formula (I).

8. The process as claimed in claim 1, wherein the R$^1$ is a methyl group or an ethyl group; R$^2$ is a methyl group or an ethyl group; and X is a hydrogen atom.

9. The process as claimed in claim 2, wherein the dialkyl sulfate is dimethyl sulfate or diethyl sulfate and said dialkyl sulfate is in an amount of 8 to 12 moles per mole of the alkylthiophenol compound of the formula (I).

10. The process as claimed in claim 9, with further comprises the reaction being carried out in the presence of a solvent selected from the group consisting of acetonitrile, ethyl acetate, dioxane and toluene, and said solvent is present in an amount of 0.1 to 10 liters per mol of the alkylthiophenol compound of the formula (I).

11. The process as claimed in claim 10, wherein the solvent is acetonitrile and is present in an amount of 0.5 to 3 liters per mole of the alkylthiophenol compound of the formula (I).

12. The process as claimed in claim 11, wherein the reaction is conducted at a temperature of 40° to 120° C.

* * * * *